(12) United States Patent
Soni et al.

(10) Patent No.: US 10,888,519 B2
(45) Date of Patent: Jan. 12, 2021

(54) IMMEDIATE RELEASE PHARMACEUTICAL COMPOSITION OF IRON CHELATING AGENTS

(71) Applicant: Jubilant Generics Limited, Uttar Pradesh (IN)

(72) Inventors: Pankaj Soni, Noida (IN); Premchand Dalichandji Nakhat, Noida (IN); Ganesh Vinayak Gat, Noida (IN); Kamal S. Mehta, Noida (IN); Dinesh Kumar, Noida (IN); Vikas Bali, Noida (IN)

(73) Assignee: Jubilant Generics Limited

(*) Notice: Subject to any disclaimer, the term of this patent is extended or adjusted under 35 U.S.C. 154(b) by 0 days.

(21) Appl. No.: 16/087,035

(22) PCT Filed: Jul. 5, 2017

(86) PCT No.: PCT/IB2017/054048
§ 371 (c)(1),
(2) Date: Sep. 20, 2018

(87) PCT Pub. No.: WO2018/007956
PCT Pub. Date: Jan. 11, 2018

(65) Prior Publication Data
US 2019/0117566 A1    Apr. 25, 2019

(30) Foreign Application Priority Data
Jul. 5, 2016 (IN) .............................. 201611022996

(51) Int. Cl.
*A61K 9/00* (2006.01)
*A61K 9/20* (2006.01)
(Continued)

(52) U.S. Cl.
CPC .......... *A61K 9/0056* (2013.01); *A61K 9/2013* (2013.01); *A61K 9/2018* (2013.01);
(Continued)

(58) Field of Classification Search
None
See application file for complete search history.

(56) References Cited

U.S. PATENT DOCUMENTS

| | | | |
|---|---|---|---|
| 2009/0142395 A1* | 6/2009 | Zadok | A61K 9/0095 424/465 |
| 2014/0147503 A1* | 5/2014 | Malhotra | A61K 9/2018 424/489 |
| 2016/0120847 A1* | 5/2016 | Malhotra | A61K 31/4196 424/489 |

OTHER PUBLICATIONS

Overview of pharmaceutical excipients used in tablets and capsules, Drug Topics, Oct. 24, 2008. (Year: 2008).*

* cited by examiner

*Primary Examiner* — Melissa S Mercier
(74) *Attorney, Agent, or Firm* — William D. Hare, Esq.; McNeely, Hare & War, LLP

(57) ABSTRACT

The present invention relates to a stable, immediate release solid oral pharmaceutical compositions comprising iron chelating agents like Deferasirox and at least one pharmaceutical acceptable excipient wherein the composition is free of glidant. Prior art discloses various technical challenges and suggest restrictive and complex solutions for the development of immediate release dosage forms of Deferasirox such as utilizing a large number of excipients or non-conventional formulation techniques. The glidant free immediate release solid oral pharmaceutical composition of Deferasirox, prepared as per present invention exhibited (Continued)

shows the overlay X-ray powder diffraction pattern of Deferasirox API, Placebo and Composition prepared as per the invention.

desirable technical attributes like pharmaceutical stability, flow properties and comparable dissolution, bioequivalence against reference listed drug.

19 Claims, 1 Drawing Sheet

(51) Int. Cl.
    *A61P 7/00*           (2006.01)
    *A61K 31/4196*     (2006.01)
    *A61K 9/28*          (2006.01)

(52) U.S. Cl.
    CPC .......... *A61K 9/2027* (2013.01); *A61K 9/2031* (2013.01); *A61K 9/2054* (2013.01); *A61K 9/2095* (2013.01); *A61K 9/288* (2013.01); *A61K 9/2893* (2013.01); *A61K 31/4196* (2013.01); *A61P 7/00* (2018.01)

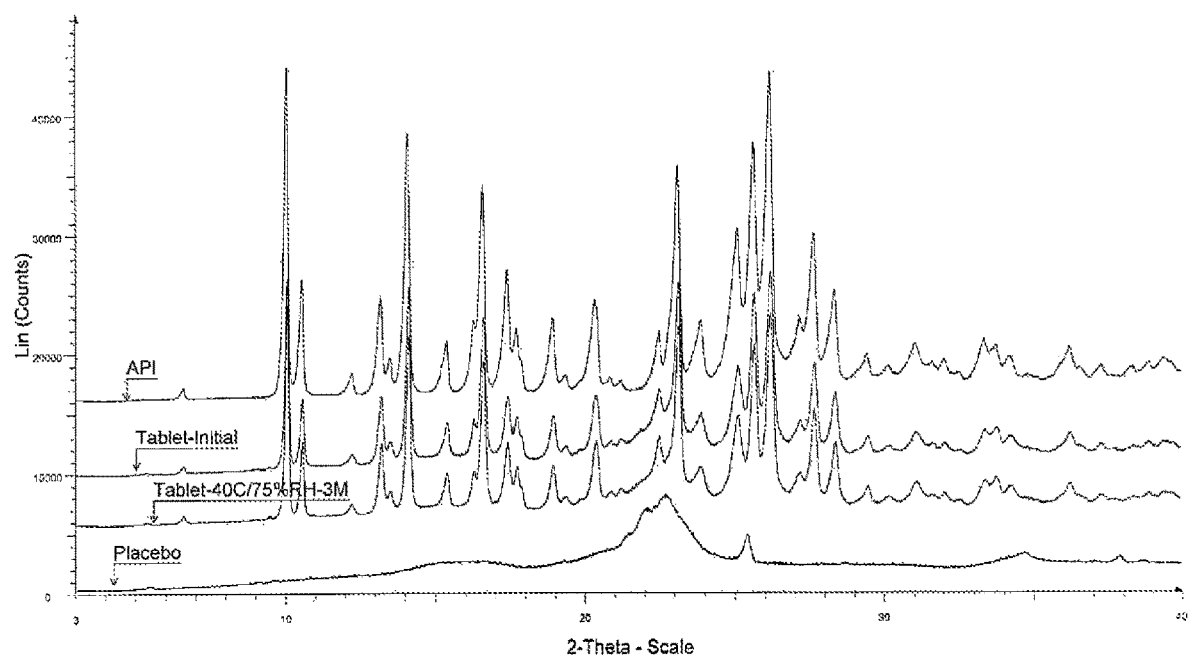
shows the overlay X-ray powder diffraction pattern of Deferasirox API, Placebo and Composition prepared as per the invention.

IMMEDIATE RELEASE PHARMACEUTICAL COMPOSITION OF IRON CHELATING AGENTS

FIELD OF THE INVENTION

This invention relates to pharmaceutical compositions comprising iron chelating agents or their pharmaceutically acceptable salts, esters, solvates, polymorphs, enantiomers or mixtures thereof. In particular, but without restriction to the particular embodiments hereinafter described in accordance with the best mode of practice, present invention provides a stable solid oral immediate release pharmaceutical composition comprising Deferasirox or its pharmaceutically acceptable salts, esters, solvates, polymorphs, enantiomers or mixtures thereof. The invention also provides a process for manufacturing and use of such composition in the treatment of chronic iron overload.

BACKGROUND OF THE INVENTION

Deferasirox is an iron chelating agent and is indicated for treatment of chronic iron overload due to blood transfusions (transfusional iron overload) and treatment of chronic iron overload in non-transfusion-dependent thalassemia syndromes. Deferasirox is chemically described as 4-[3,5-bis (2-hydroxyphenyl)-1H-1,2,4-triazol-1-yl]benzoic acid and is represented by the following formula:

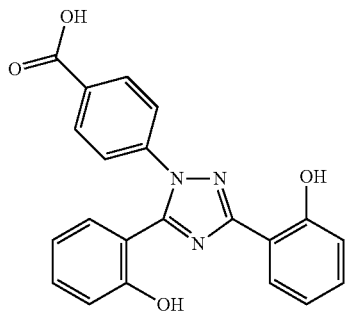 [SMILES: O=C(O)c1ccc(-n2nc(-c3ccccc3O)nc2-c2ccccc2O)cc1]

U.S. Pat. No. 6,465,504 assigned to Novartis AG describes 3,5-diphenyl-1,2,4-triazoles including Deferasirox and a process for the preparation of Deferasirox. This patent publication also teaches use of 3,5-diphenyl-1,2,4-triazoles derivatives as iron chelators which can be used for the treatment of iron overload in warm-blooded animals.

Deferasirox is poorly soluble in water and accordingly reported as BCS class II molecule, which leads to poor dissolution and administration of high dose of the drug to attain desired therapeutic effect. Various formulation technical challenges associated with Deferasirox like poor aqueous solubility, dissolution, disintegration, flowability and compressibility of the high dose drug also offer manufacturing challenges to a formulation scientist in developing a suitable formulation of Deferasirox. Deferasirox is also known to exhibit polymorphism accordingly control of polymorphs during the formulation developent is also important.

Deferasirox was approved in USA on Nov. 2, 2005 as a Tablet for oral suspension (dispersible tablet) under the brand name EXJADE® in strengths of 125 mg, 250 mg and 500 mg. Inactive ingredients in the EXJADE® tablet for suspension include lactose monohydrate, crospovidone, povidone (K30), sodium lauryl sulphate, microcrystalline cellulose, silicon dioxide, and magnesium stearate.

U.S. Patent Publication Nos. US 2008/0312302, US 2006/110446, US 2008/311194, US 2011/046193, US 2011/319457 US 2012/196909 and US 2016/0175255 assigned to Novartis disclose dispersible tablet formulation of Deferasirox prepared by wet granulation method. These patent publications highlight the technical challenges encountered with Deferasirox such as sticking and poor flow characteristics which adversely impact manufacturability of the dosage form.

Other patent and patent publications like WO 2009/106824, U.S. Pat. No. 8,703,203, IN 2729/CHE/2012, WO 2014/067501, WO 2010/035282, WO 2016/028245, US 2009/0142395, EP2946771A1 also disclose dispersible tablet dosage form of Deferasirox.

U.S. Patent Publication Nos. US 2016/0120847 and US 2016/0158202 assigned to Cipla disclose a low dose pharmaceutical composition comprising Deferasirox and one or more pharmaceutically acceptable excipients. The invention utilizes nano-sized Deferasirox for the preparation of low dose pharmaceutical composition comprising Deferasirox.

US 2015/0017241 highlight that dispersible tablets of Deferasirox is known to cause Gastro Intestinal Irritation and kidney toxicity, upper Gastro Intestinal ulceration, multiple ulceration and hemorrhage in some patients (especially children and adolescents). Dispersible tablets also cause local accumulation of drug content as they limit the direct contact of drug compound with stomach mucosa which may often lead to stomach bleeding. Further, dispersible tablets also possess poor patient compliance since they need to be taken on an empty stomach at least 30 minutes before food and stirred in an appropriate amount of water, orange juice, or apple juice until a fine suspension is obtained prior to administration.

For these reason, dispersible tablet dosage form of Deferasirox is less preferred and to overcome these challenges Deferasirox later re-formulated and was approved in the USA on Mar. 30, 2015 as an immediate release tablet oral dosage form under the brand name JADENU® 90 mg, 180 mg and 360 mg tablets. Inactive ingredients in JADENU® tablets include microcrystalline cellulose, crospovidone, povidone (K30), magnesium stearate, colloidal silicon dioxide, poloxamer (188) and film coating. The marketed formulation contains a glidant like colloidal silicon dioxide.

U.S. Patent Publication No. US 2015/0017241 and Publication No. US 2016/0220493 assigned to Novartis AG discloses non-dispersible dosage form with drug load of about 55.56% (w/w) and use at least one filler (about to 10% to 40%), disintegrant (about 1% to 10%), binder (about 1% to 5%), surfactant (about 0.0% to 2%), glidant (about 0.1% to 1%) or lubricant (about 0.1% to 2%). The technical disclosure made in these patent publications suggest use of glidant like silicone dioxide to achieve desired pharmaceutical technical attribute.

The pharmaceutical compositions of Deferasirox suitable for oral administration to humans must have desirable chemical and physical properties, disintegration, dissolution, stability and bioequivalence complying with demanding requirements and regulations of health and medicine regulatory agencies across the world, especially USFDA, EMEA, MHRA, PMDA, Health Canada, ANVISA and TGA.

The prior art discloses complex approaches for formulating Deferasirox into suitable dosage form like: a) use of extrusion-spheronization technique; b) use of glidants to improve flow properties; c) use of nano-sized Deferasirox. Extrusion-spheronisation is a relatively complex technique wherein the process requires specialized equipment that generates compacted cylindrical strands from the wet mass. Further, use of these techniques is very common in the pharmaceutical technology to produce spheronized granules/pellets for improving flow characteristics.

Thus, there is a need of an alternate immediate release solid oral dosage form of Deferasirox with desirable technical formulation attributes such as disintegration, dissolution, improved flow characteristics such as bulk density, tapped density, Hausner ratio, compressibility index, stability, bioequivalence and which can be prepared by a simple, reproducible and commercially viable process.

The present inventors have surprisingly developed a simple, reproducible, cost-effective and stable alternate dosage form of Deferasirox which offers desirable technical attributes such as disintegration, dissolution, improved flow characteristics such as bulk density, tapped density, Hausner ratio, compressibility index, stability, bioequivalence comparable to the commercially available counterpart (JADENU® Tablets). Further, the process employed for manufacturing of immediate release dosage form of Deferasirox is consistent and therefore feasible for industrial production.

OBJECTS AND SUMMARY OF THE INVENTION

It is a principal object of the present invention to provide a stable, immediate release high drug load pharmaceutical composition comprising Deferasirox or its pharmaceutically acceptable salts, esters, solvates, polymorphs, enantiomers or mixtures thereof with one or more pharmaceutically acceptable excipient and/or carrier.

It is another object of the present invention to provide a process for the preparation of stable high drug load pharmaceutical composition comprising Deferasirox or its pharmaceutically acceptable salts, esters, solvates, polymorphs, enantiomers or mixtures thereof.

It is another object of the present invention to provide a stable solid pharmaceutical composition in form of a tablet or granule for oral administration comprising Deferasirox with one or more pharmaceutically acceptable excipient and/or carrier and process for their preparation.

It is another object of the present invention to provide a stable solid pharmaceutical composition in form of a tablet or granule for oral administration comprising Deferasirox with one or more pharmaceutically acceptable excipient and/or carrier like diluent, binder, disintegrant, surfactant, lubricant, pH adjusting agents, coloring agent, sweetening agents, flavoring agent, buffers, and other pharmaceutical excipients.

Another object of the present invention is to develop a tablet or granule for oral administration comprising Deferasirox by a manufacturing process which is consistent and therefore feasible for industrial production, while maintaining stability and pharmaceutical equivalence to the reference listed drug.

The following embodiments further describe the objects of the present invention in accordance with the best mode of practice, however, disclosed invention is not restricted to the particular embodiments hereinafter described.

In accordance with a preferred embodiment of the present invention, there is provided a stable immediate release solid oral pharmaceutical compositions comprising Deferasirox or its pharmaceutically acceptable salts, esters, solvates, polymorphs, enantiomers or mixtures thereof with one or more pharmaceutically acceptable excipient and/or carrier, wherein the composition is free of glidant.

In accordance with another embodiment of the present invention, there is provided a stable immediate release solid oral pharmaceutical compositions comprising Deferasirox or its pharmaceutically acceptable salts, esters, solvates, polymorphs, enantiomers or mixtures thereof with one or more pharmaceutically acceptable excipient and/or carrier, wherein the composition is free of colloidal silicon dioxide.

In accordance with another embodiment of the present invention, there is provided a stable immediate release solid pharmaceutical tablet or granule composition Deferasirox or its pharmaceutically acceptable salts, esters, solvates, polymorphs, enantiomers or mixtures thereof and a pharmaceutically acceptable excipient selected from at least one of diluent, binder, disintegrant, surfactant, wetting agent, lubricant, pH adjusting agents, coloring agent, sweetening agent, flavoring agent and/or buffer.

In accordance with yet another embodiment of the present invention, there is provided a stable solid oral pharmaceutical composition in the form of an immediate release tablet or granule comprising Deferasirox or its pharmaceutically acceptable salts, esters, solvates, polymorphs, enantiomers or mixtures thereof, wherein composition is substantially free of surfactant.

In accordance with one other embodiment of the present invention, there is provided a solid oral pharmaceutical composition in the form of a stable immediate release tablet or granule comprising Deferasirox or its pharmaceutically acceptable salts, esters, solvates, polymorphs, enantiomers or mixtures thereof, wherein the intra-granular part of the composition is free of any dry binder and/or extra-granular part of the composition is free of binder.

In accordance with yet another embodiment of the present invention, there is provided a stable solid oral pharmaceutical composition in the form of an immediate release tablet or granule comprising Deferasirox or its pharmaceutically acceptable salts, esters, solvates, polymorphs, enantiomers or mixtures thereof, wherein the disintegrant is present in an equal amount and/or distributed in an ratio 0.5:1 to 1:1 of intra-granular to extra-granular part of composition In accordance with yet another embodiment of the present invention, there is provided a stable solid oral pharmaceutical composition comprising Deferasirox or its pharmaceutically acceptable salts, wherein the composition is not an enteric coated (does not contain any enteric coated polymer such as polymethacylates; Eudragit®) or a dispersible tablet dosage form.

In accordance with still another embodiment of the present invention, there is provided a stable pharmaceutical composition comprising granules of Deferasirox or its pharmaceutically acceptable salts and at least one or more pharmaceutically acceptable excipient including a binder, a disintegrant, a surfactant and/or wetting agent and a lubricant, wherein a) intra-granular part of the composition free of any dry binder b) extra-granular part of the composition is free of binder c) disintegrant is present in an equal amount of intra-granular and/or in extra-granular part of composition, wherein the composition is free of any glidant.

In accordance with still another embodiment of the present invention, the compositions of present invention results in an increase in the bulk density (from about 0.185 g/mL in the API prior to granulation to around 0.3-0.5 g/mL in composition), improved Hausner Ratio (from about 1.62 to around 1.293), improved Compressibility Index (from about 38.33% to around 22.682%) in the mixture of drug and excipients, for example by compression to form a tablet or granule dosage form.

In accordance with still another embodiment of the present invention, there is provided a stable pharmaceutical composition comprising Deferasirox prepared by wet granulation, dry granulation, dry blending, dry mixing or direct compression process.

In accordance with still another embodiment of the present invention, there is provided a process for the preparation of a stable pharmaceutical composition comprising Deferasirox or its pharmaceutically acceptable salts, esters, solvates, polymorphs, enantiomers or mixtures thereof comprising the steps of a) Sifting the accurately weighed quantities of active agent and one or more pharmaceutically acceptable excipient(s) through a suitable sieve followed by mixing; b) Granulating the mixture of step a) with a binder solution (aqueous or non-aqueous solvent); c) Drying the granulated mass, optionally milling of the dried granules; d) optionally mixing with other pharmaceutical acceptable excipients to prepare granule dosage form or optionally compressing the granules to form tablets.

In accordance with still another embodiment of the present invention, there is provided a stable solid oral pharmaceutical composition comprising a pharmacologically effective amount of Deferasirox or its pharmaceutically acceptable salts, esters, solvates, polymorphs, enantiomers or mixtures thereof, wherein the composition exhibits desirable disintegration, dissolution, improved flowability and compressibility to the reference listed drug.

In accordance with still another embodiment of the present invention, there is provided a stable solid oral pharmaceutical composition in the form of an immediate release tablet or granule comprising Deferasirox or its pharmaceutically acceptable salts, esters, solvates, polymorphs, enantiomers or mixtures thereof wherein, the composition comprises from about 20% to about 80% by weight of Deferasirox based on the total weight of the composition.

In accordance with still another embodiment of the present invention, there is provided a stable solid oral pharmaceutical composition in the form of an immediate release tablet or granule comprising Deferasirox or its pharmaceutically acceptable salts, esters, solvates, polymorphs, enantiomers or mixtures thereof wherein, the composition comprises from about 20 mg to 800 mg of Deferasirox.

In accordance with still another embodiment of the present invention, there is provided a stable solid oral pharmaceutical composition in the form of an immediate release tablet or granule comprising Deferasirox or its pharmaceutically acceptable salts, esters, solvates, polymorphs, enantiomers or mixtures thereof includes particle size of Deferasirox, wherein $D_{90}$ is less than 100 μm.

In accordance with still another embodiment of the present invention, there is provided a high drug load pharmaceutical composition which is stable at 40° C. and 75% relative humidity.

In accordance with still another embodiment of the present invention, there is provided a stable immediate release solid oral pharmaceutical compositions comprising Deferasirox or its pharmaceutically acceptable salts, esters, solvates, polymorphs, enantiomers or mixtures thereof, wherein the composition is substantially free from other polymorphic forms.

In accordance with still another embodiment of the present invention, there is provided use of immediate release solid oral pharmaceutical composition comprising Deferasirox or its pharmaceutically acceptable salts, esters, solvates, polymorphs, enantiomers or mixtures thereof in the treatment of chronic iron overload due to blood transfusions.

BRIEF DESCRIPTION OF THE DRAWINGS

The above and other objects and features of the present invention will become apparent from the following description of the invention, when taken in conjunction with the accompanying drawings, in which:

FIG. 1 shows the overlay X-ray powder diffraction pattern of Deferasirox API, Placebo and Composition prepared as per the invention.

DESCRIPTION OF THE INVENTION

The present invention can be more readily understood by reading the following detailed description of the invention and study of the included examples.

As used herein, the term "composition", as in pharmaceutical composition, is intended to encompass a drug product comprising Deferasirox or its pharmaceutically acceptable salts, esters, solvates, polymorphs, enantiomers or mixtures thereof, and the other inert ingredient(s). Such pharmaceutical compositions are synonymous with "formulation" and "dosage form". Pharmaceutical compositions of the invention include, but are not limited to, granules, tablets, modified release tablets, capsules (immediate or modified release), sachets, powders, mini-tablets and the like. Preferably, the pharmaceutical composition refers to tablets (uncoated or film coated) or granule.

The term "excipient" means a pharmacologically inactive component such as a diluent, lubricant, surfactant, carrier, or the like. The excipients that are useful in preparing a pharmaceutical composition are generally safe, non-toxic and are acceptable for veterinary as well as human pharmaceutical use. Reference to an excipient includes both one and more than one such excipient. Co-processed excipients are also covered under the scope of present invention.

"Substantially free" as used herein refers to the pharmaceutical composition of Deferasirox comprises less than 0.1% w/w binder and/or surfactant by total weight of the composition.

As used herein, the term "intra-granular" (part/phase/portion) refers to the components of formulation of the present invention that are within granules. As used herein, the term "extra-granular" (part/phase/portion) refers to those components of formulation of the present invention that are outside the granules.

Unless otherwise stated the weight percentages expressed herein are based on the final weight of the composition or formulation.

As used herein, the term "Deferasirox" is used in broad sense to include not only "Deferasirox" per se but also its pharmaceutically acceptable salts, pharmaceutically acceptable solvates, pharmaceutically acceptable hydrates, pharmaceutically acceptable enantiomers, pharmaceutically acceptable derivatives, pharmaceutically acceptable isomers, pharmaceutically acceptable polymorphs, pharmaceutically acceptable prodrugs thereof, and also its various crystalline and amorphous forms. The term "Deferasirox" used in this specification means in substantially pure form, i.e. at least about 97% pure. The term "high drug load" as used herein, refers from about 20% to about 80% by weight of Deferasirox based on the total weight of the composition.

The term "immediate release" as used herein, refers to any type of release of the active ingredient from the composition of the present invention resulting in in-vitro release over a short period of time, i.e., (less than one hour). Preferably, more than 85% of drug is released within 20 minutes.

The pharmaceutical compositions of present invention comprise about 20 mg to about 800 mg of Deferasirox, preferably about 90 to about 360 mg of Deferasirox. The pharmaceutical composition comprises Deferasirox in the range of about 20% to about 80% by weight on the basis of the total weight of the composition.

In another embodiment the immediate release solid oral pharmaceutical composition of the present invention includes particle size of Deferasirox or its pharmaceutically acceptable salts, esters, solvates, polymorphs, enantiomers or mixtures thereof, wherein $D_{90}$ is less than 100 µm. Particle size reduction can be performed by techniques including but not limited to fluid energy milling, ball milling, colloid milling, roller milling, hammer milling and the like. Particle size and particle size distribution can be measured by techniques such as Laser light scattering (e.g. Malvern Light Scattering), Coulter counter, microscopy and the like.

In another embodiment of the present invention, immediate release stable solid oral pharmaceutical compositions comprising Deferasirox or its pharmaceutically acceptable salts, esters, solvates, polymorphs, enantiomers or mixtures thereof, wherein the composition is substantially free from other polymorphic forms.

In another embodiment of the invention, the pharmaceutical composition comprising Deferasirox or its pharmaceutically acceptable salts, esters, solvates, polymorphs, enantiomers or mixtures thereof is prepared by wet or dry process. The wet and dry processes include, but are not limited to, wet granulation, dry granulation, dry blending, dry mixing and direct compression. Other formulation techniques are also contemplated within the scope of the present invention. Any pharmaceutically acceptable granulating agent can be used for wet granulation. Preferable granulating solvents include, but are not limited to, water, esters such as ethyl acetate; ketones such as acetone; alcohols such as methanol, ethanol, isopropanol, butanol; dichloromethane, chloroform, dimethyl acetamide (DMA), dimethyl sulfoxide (DMSO), ether, diethyl ether and combinations thereof.

In another embodiment of the invention, wet granulation can be performed using Rapid mixer granulator, Fluid bed granulator, Planetary mixer and the like; dry blending can be performed using V-blender or key blender; and dry granulation can be performed using roller compacter or slugging techniques or by any other method known in the art.

In another embodiment of the invention, there is provided a process for the preparation of a stable pharmaceutical composition comprising Deferasirox or its pharmaceutically acceptable salts, esters, solvates, polymorphs, enantiomers or mixtures thereof comprising the steps of a) Sifting the accurately weighed quantities of active agent and one or more pharmaceutically acceptable excipient(s) through a suitable sieve followed by mixing; b) Granulating the mixture of step a) with a binder solution (aqueous or non-aqueous solvent); c) Drying the granulated mass, optionally milling of the dried granules; d) optionally mixing with other pharmaceutical acceptable excipients to prepare granule dosage form or optionally compressing the granules to form tablets.

In another embodiment of the invention, there is provided a process for preparation of immediate release dosage form of Deferasirox wherein the process is easily scalable at an industrial scale.

In another embodiment of the present invention there is provided a stable solid oral pharmaceutical composition comprising Deferasirox with one or more pharmaceutically acceptable excipient and/or carrier like diluent, binder, disintegrant, surfactant, wetting agent, lubricant, pH adjusting agents, coloring agent, sweetening agents, flavoring agent, buffers, and other pharmaceutical excipients.

Embodiments of the present invention relate to a stable immediate release solid oral pharmaceutical compositions comprising Deferasirox or its pharmaceutically acceptable salts, esters, solvates, polymorphs, enantiomers or mixtures thereof with one or more pharmaceutically acceptable excipient and/or carrier, wherein the composition is free of glidant.

Embodiments of the present invention relate to a stable immediate release solid oral pharmaceutical compositions comprising Deferasirox or its pharmaceutically acceptable salts, esters, solvates, polymorphs, enantiomers or mixtures thereof with one or more pharmaceutically acceptable excipient and/or carrier, wherein the composition is free of colloidal silicon dioxide.

Embodiments of the present invention relate to solid oral pharmaceutical composition comprising Deferasirox or its pharmaceutically acceptable salts, esters, solvates, polymorphs, enantiomers or mixtures thereof, wherein the composition is not a enteric coated (does not contain any enteric coated polymer such as polymethacylates; Eudragit®) or a dispersible tablet.

Embodiments of the present invention also relate to a stable solid oral pharmaceutical composition in the form of an immediate release tablet or granule comprising Deferasirox or its pharmaceutically acceptable salts, esters, solvates, polymorphs, enantiomers or mixtures thereof, wherein composition is substantially free of surfactant.

Embodiments of the present invention also relate to a stable solid oral pharmaceutical composition in the form of an immediate release tablet or granule comprising granules of Deferasirox or its pharmaceutically acceptable salts, esters, solvates, polymorphs, enantiomers or mixtures thereof, wherein the intra-granular part of the composition is free of any dry binder and/or extra-granular part of the composition is free of binder.

Embodiments of the present invention also relate to a stable solid oral pharmaceutical composition in the form of an immediate release tablet or granule comprising Deferasirox or its pharmaceutically acceptable salts, esters, solvates, polymorphs, enantiomers or mixtures thereof, wherein disintegrant is present in an equal amount and/or distributed in an ratio 0.5:1 to 1:1 of intra-granular to extra-granular part of composition Embodiments of the present invention also relate to pharmaceutical composition comprising granules of Deferasirox or its pharmaceutically acceptable salts, esters, solvates, polymorphs, enantiomers or mixtures thereof and at least one or more pharmaceutically acceptable excipient including a binder, a disintegrant, a surfactant and/or wetting agent and a lubricant, wherein a) intra-granular part of the composition free of any dry binder b) extra-granular part of the composition is free of binder c) disintegrant is present in an equal amount of intra-granular and/or in extra-granular part of composition, wherein the composition is free of any glidant.

Embodiments of the present invention also relate to a stable solid oral pharmaceutical composition of Deferasirox or its pharmaceutically acceptable salts, esters, solvates, polymorphs, enantiomers or mixtures thereof, and at least one or more pharmaceutically acceptable excipient, wherein the composition exhibits more than 85% of drug release within 20 minutes in 900 ml of Phosphate Buffer, pH 6.8 having 0.5% Tween 20 (Office of Generic Drugs dissolution database) using a USP II apparatus (paddle) at a temperature of 37±0.5° C. and a rotation speed of 75 revolutions per minute.

The composition of present invention were analyzed for bulk and tapped density and flow properties such as Hausner Ratio, Compressibility Index. Bulk Density and Tapped Density is determined using the standard method of Test 616 (Bulk Density and Tapped Density) of USP 32. The Hausner ratio may be calculated using formula $p_{tap}/p_{bulk}$ where $p_{tap}$ represents tapped density of granulate mass and $p_{bulk}$ represents the loose bulk density of granulate mass. A Hausner ratio of <1.25 indicates a powder that is free flowing whereas >1.25 indicates poor flowability. Compressibility index is indirect measure of the flowability of the powder and it is determined according to US Pharmacopeia General Chapter <1174>. The smaller the compressibility index the better the flow properties. For example 5-15 indicates excellent, 12-16 good, 18-21 fair and >23 poor flow.

Various useful fillers or diluents include, but are not limited to calcium carbonate, calcium phosphate, dibasic anhydrous, calcium phosphate, dibasic dihydrate, calcium phosphate tribasic, calcium sulphate, cellulose powdered, silicified microcrystailine cellulose, cellulose acetate, compressible sugar, confectioner's sugar, dextrates, dextrose, fructose, lactitol, lactose, magnesium carbonate, magnesium oxide, maltodextrin, maltose, mannitol, microcrystailine cellulose, polydextrose, simethicone, sodium alginate, sodium chloride, sorbitol, starch, pregelatinized starch, sucrose, trehalose and xylitol, or mixtures thereof. Preferably, filler is used in an amount of from about 1% to about 90% by weight. More preferably, the amount of diluent(s) may vary within a range of from about 0% to less than about 75% by weight based on the total weight of the composition.

Various useful binders include, but are not limited to acacia, alginic acid, carbomer, carboxymethylcellulose sodium, *ceratonia*, cottonseed oil, dextrin, dextrose, gelatin, guar gum, hydrogenated vegetable oil type 1, hydroxyethyl cellulose, hydroxyethyhnethyl cellulose, hydroxypropyl cellulose, low substituted hydroxypropyl cellulose, hypromellose, magnesium aluminium silicate, maltodextrin, maltose, methylcellulose, microcrystalline cellulose, polydextrose, polyethylene oxide, povidone, sodium alginate, starch, pregelatinised starch, stearic acid, sucrose and zein, or mixtures thereof. The amount of binder(s) may vary within a range of from about 0% to about 10% by weight based on the total weight of the composition. Preferably, binder is optionally used in an amount of about 0% to less than about 5% by weight.

Various useful disintegrants include, but are not limited to, alginic acid, calcium phosphate, tribasic, carboxymethylcellulose calcium, carboxymethylcellulose sodium, croscarmellose sodium, crospovidone, docusate sodium, guar gum, low substituted hydroxypropyl cellulose, magnesium aluminun silicate, methylcellulose, microcrystalline cellulose, povidone, sodium alginate, sodium starch glycolate, polacrilin potassium, silicified microcrystalline cellulose, starch or pre-gelatinized starch, or mixtures thereof. The amount of disintegrant(s) may vary within a range of from about 0% to about 15% by weight based on the total weight of the composition. Preferably, disintegrant is optionally used in an amount of about 0% to less than about 5% by weight.

Lubricants used in the composition include, but are not limited to, calcium stearate, glycerine monostearate, glyceryl behenate, glyceryl palmitostearate, hydrogenated castor oil, hydrogenated vegetable oil 0 type I, magnesium lauryl sulphate, magnesium stearate, medium-chain triglycerides, poloxamer, polyethylene glycol, sodium benzoate, sodium chloride, sodium lauryl sulphate, sodium stearyl fumarate, stearic acid, talc, sucrose stearate and zinc stearate or mixtures thereof. Preferably, lubricant is present in an amount of about 0% to about 5% by weight. More preferably, lubricant is present in an amount of about 0.1% to less than about 2% by weight.

Glidants improve flowability and accuracy of dosing. However, known glidants like tribasic calcium phosphate and colloidal silicon dioxide are not present in the compositions prepared as per present invention.

Various directly compressible grades of pharmaceutically acceptable excipients are also contemplated within the scope of the present invention. Directly compressible excipients include but are not limited to anhydrous lactose, spray dried lactose, dibasic calcium phosphate dihydrate, microcrystalline cellulose, powdered cellulose, low substituted hydroxypropyl cellulose, dextrose, sucrose, modified dextrin+sucrose, spray dried maltose, maltodextrin, mannitol, xylitol, sorbitol, lactitol, starch, pregelatinized starch etc.

Surfactants or surface-active agents improve wettability of the dosage form and/or enhance its dissolution. Surfactants contemplated in the present invention include but are not limited to anionic surfactants, amphoteric surfactants, non-ionic surfactants and macromolecular surfactants. Suitable examples of surfactants include but are not limited to sodium lauryl sulphate, sodium cetyl stearyl sulphate or sodium dioctyl sulphosuccinate, lecithin, cetyl alcohol, stearyl alcohol, cetyl stearyl alcohol, cholesterol, sorbitan fatty acid esters such as sorbitan mono-oleate, polyoxyethylene sorbitan fatty acid esters such as polysorbate 20, polyoxyethylene fatty acid glycerides such as macrogol 1000 glycerol monostearate, polyoxyethylene fatty acid esters such as polyoxyl 40 stearate, polyoxyethylene fatty alcohol ethers such as polyoxyl 10 oleyl ether, glycerol fatty acid esters such as glycerol monostearate. Suitable example of a macromolecular surfactant include but is not limited to Poloxamer. Preferably, the surfactant is used in an amount of about 0% to less than about 5% by weight.

Various film forming agents include but are not limited to cellulose derivatives such as soluble alkyl- or hydroalkyl-cellulose derivatives such as methylcellulose, hydroxymethyl cellulose, hydroxyethyl cellulose, hydroxypropyl cellulose, hydroxymethylethyl cellulose, hydroxypropyl methylcellulose, sodium carboxymethyl cellulose, etc., acidic cellulose derivatives such as cellulose acetate phthalate, cellulose acetate trimellitate, and methylhydroxypropylcellulose phthalate, polyvinyl acetate phthalate, etc., insoluble cellulose derivative such as ethylcellulose and the like, dextrins, starches and starch derivatives, polymers based on carbohydrates and derivatives thereof, natural gums such as gum arabic, xanthans, alginates, polyvinyl alcohol, polyvinyl acetate, polyvinylpyrrolidone, chitosan and derivatives thereof, shellac and derivatives thereof, waxes and fat substances.

If desired, the films may contain additional adjuvants for coating such as plasticizers, polishing agents, colorants, pigments, antifoaming agents, opacifiers, and the like. As an alternative to the above coating ingredients, pre-formulated coating products such as Opadry™ may be used. The products that are sold in dry form require only mixing with a liquid before use.

The process of the present invention besides being simple, reproducible, cost-effective and stable alternate dosage form of Deferasirox which offers desirable technical attributes such as disintegration, dissolution, improved flow characteristics such as bulk density, tapped density, Hausner ratio, compressibility index, stability, bioequivalence comparable to the commercially available counterpart (JADENU® Tablets). Further, the process employed in the manufacture of immediate release dosage form of Deferasirox is consistent and therefore feasible for industrial production.

In another embodiment, pharmaceutical composition of the present invention particularly tablet dosage form of present invention can be packaged in HDPE bottles or blister packs. HDPE bottles may optionally contain desiccants.

The dosage forms prepared by the above process can be tested for physical parameters such as weight variation, hardness, disintegration test, friability etc. Several devices can be used to test tablet hardness such as a Monsanto tester, a Strong-Cobb tester, a Pfizer tester, an Erweka tester, a Schleuniger tester, etc. Friability can be determined using a Roche friabilator for 100 revolutions at 25 rpm. Disintegration time testing for tablets can be performed in a USP tablet disintegration tester wherein a tablet is placed in a basket, which moves upward and downward in a 1 litre beaker of water at 37° C.

The oral tablet dosage form prepared by the above process can be subjected to in vitro dissolution evaluation according to Test 711 "Dissolution" in the United States Pharmacopoeia 37, United States Pharmacopoeial Convention, Inc., Rockville, Md., 2014 ("USP") to determine the rate at which the active substance is released from the dosage form, and the content of the active substance can be determined in solution by high performance liquid chromatography. When comparing the test and reference products, dissolution profiles should be compared using a similarity factor ($f_2$). The similarity factor is a logarithmic reciprocal square root transformation of the sum of squared error and is a measurement of the similarity in the percent (%) of dissolution between the two curves.

$$f_2 = 50 \cdot \log \left\{ [1 + (1/n) \Sigma_{t=1}^{n} (R_t - T_t)^2]^{-0.5} \cdot 100 \right\}$$

Two dissolution profiles are considered similar when the $f_2$ value is equal to or greater than 50.

In another embodiment, solid oral pharmaceutical composition of the present invention exhibits more than 85% of drug release within 20 minutes in 900 ml of Phosphate Buffer, pH 6.8 having 0.5% Tween 20 (Office of Generic Drugs dissolution database) using a USP II apparatus (paddle) at a temperature of 37±0.5° C. and a rotation speed of 75 revolutions per minute.

As used herein, the term "about" means±approximately 20% of the indicated value, such that "about 10 percent" indicates approximately 08 to 12 percent.

In accordance with still another embodiment of the present invention, there is provided use of immediate release solid oral pharmaceutical composition comprising Deferasirox or its pharmaceutically acceptable salts, esters, solvates, polymorphs, enantiomers or mixtures thereof in the treatment of chronic iron overload due to blood transfusions.

Having described the invention with reference to certain preferred embodiments, other embodiments will become apparent to one skilled in the art from consideration of the specification. The invention is further defined by reference to the following examples describing in detail method for the preparation and testing of Deferasirox pharmaceutical composition. It will be apparent to those skilled in the art that many modifications, both to materials and methods, may be practiced without departing from the scope of the invention. Following examples are set out to illustrate the invention and do not limit the scope of the present invention.

EXAMPLES

The following examples are intended to further illustrate certain preferred embodiments of the invention and are not limiting in nature.

Example I

Deferasirox Tablets were prepared quantitative formula as given in Table 1:

TABLE 1

| | | Example I | | | |
|---|---|---|---|---|---|
| Ingredients | Role of Excipient | I-A % (w/w) | I-B % (w/w) | I-C % (w/w) | I-D % (w/w) |
| Deferasirox | API | 60 | 68 | 74 | 71.5 |
| Microcrystalline Cellulose | Diluent/Filler | — | 18 | 18.63 | — |
| Lactose | Diluent/Filler | 24.54 | — | — | 18 |
| Crospovidone | Disintegrant | 7.49 | 7.6 | 4.89 | 4.03 |
| Poloxamer | Wetting agent | 0.18 | 0.18 | 0.12 | — |
| Povidone | Binder | 5.29 | 4.89 | — | 4.11 |
| Magnesium Stearate | Lubricant | 2.5 | 2.1 | 2.42 | 2.47 |
| Core Total Weight | | 100 | 100 | 100 | 100 |
| Opadry | Film coat | 2.5-3.00 | 2.5-3.00 | 2.5-3.00 | 2.5-3.00 |
| Purified water | | q.s. | q.s. | q.s. | q.s. |

Procedure:
  i) Deferasirox and other excipients were sifted through a suitable sieve. The sifted blend was mixed for a suitable time.
  ii) Binder solution was prepared by dissolving binder and optionally surfactant in water.
  iii) Step i) blend was granulated using step ii) binder solution.
  iv) The granules of step iii) were dried and the dried granules were sifted/milled through a suitable sieve/mill.
  v) The milled material was optionally mixed with other excipients and lubricated with lubricant.
  vi) The blend of step v) was prepare as granule dosage form or optionally compressed into tablets using suitable punches.
  vii) The tablets of step vii) were optionally film coated.

Example II

Disintegration time of the tablet dosage form prepared using quantitative composition as given in Example I-B was evaluated in a USP tablet disintegration tester wherein the tablets were placed in a basket, which moves upward and downward in a 1 L beaker of water at 37° C. Disintegration time of the tablet dosage form prepared using quantitative composition as given in Example I-B was found to be in range of 3 to 5 minutes.

Example III

The standardized method and equipment for testing dissolution time is provided in Office of Generic Drugs dissolution database. The dissolution profile of tablet dosage form prepared using quantitative composition as given in Table 1 was measured in 900 ml of Phosphate Buffer, pH 6.8 having 0.5% Tween 20 (Office of Generic Drugs dissolution database) using a USP II apparatus (paddle) at a temperature of 37±0.5° C. and a rotation speed of 75 revolutions per minute. The dissolution test was conducted on the reference formulation JADENU® oral tablets in comparison to a tablet dosage form as given in Example II. The dissolution data is provided in Table 3.

TABLE 3

| Time point | % drug released | |
|---|---|---|
| (minutes) | JADENU ® | Example I-B |
| 10 | 80 | 98 |
| 15 | 87 | 99 |
| 20 | 90 | 100 |
| 30 | 92 | 100 |
| 45 | 95 | 100 |

As, both commercially available JADENU® oral tablets and tablet dosage form prepared using quantitative composition as given in Example II exhibited more than 85% of drug release within 20 minutes, dissolution profiles of the two formulations were found to be similar.
Results:

TABLE 4

| Elements | Active Pharmaceutical Ingredient | Results (Example I-B Formulation) |
|---|---|---|
| Bulk Density | 0.185 g/ml | 0.467 g/ml |
| Tapped Density | 0.300 g/ml | 0.604 g/ml |
| Hausner Ratio | 1.62 (Very Poor) | 1.293 |
| Compressibility Index (%) | 38.33% (Very Poor) | 22.682% |

Example IV

Tablet dosage form prepared in Example I-B was subjected to Accelerated stability testing as per the ICH guidelines at temperature/relative humidity of 40°±2° C./75%±5% RH for 3 months. The tablet dosage form was placed in a high density polyethylene (HDPE) bottle with induction sealing and analyzed for drug content by High Performance Liquid Chromatography (HPLC) method. The prepared dosage form was found to be stable and exhibited following assay values (in Table 4):

TABLE 5

| Study Period | Acceptable limits | Amount of Deferasirox acetate in the Tablet dosage form |
|---|---|---|
| Initial | 90%-110% | 99.4 |
| After Three months | 90%-110% | 99.9 |

Example V

Two products are considered to be bioequivalent if the 90% confidence interval (CI) of the relative mean $C_{max}$, $AUC_{(0-t)}$ and $AUC_{(0-\infty)}$ of the test to reference should be within 80.00% to 125.00% in the fed state. A bioequivalence study comparing the tablet dosage forms prepared in Example I-B (Test product, T) with commercially available Reference product JADENU® Tablets (Reference product, R) was performed seventeen (fed study) healthy adult human subjects and plasma drug concentrations were determined at regular intervals after dosing. The following parameters were calculated for test and reference product:
$AUC_{0-t}$=Area under plasma drug concentration versus time curve, from time zero (drug administration) to the last measurable concentration.
$AUC_{0-inf}$=Area under the plasma drug concentration versus time curve, from time zero to infinity.
$T_{max}$=Time after dosing until the maximum measured plasma drug concentration.
$C_{max}$=Maximum plasma drug concentration.
T/R (Test vs Reference) ratio was determined for the calculated pharmacokinetic parameters and is tabulated in Table 6

TABLE 6

| Type of Study | Pharmacokinetic Parameter | T/R Ratio (%) | 90% Confidence Intervals for T1/R Ratio (%) |
|---|---|---|---|
| Fed Study | $C_{max}$ | 101.52 | 95.86-107.51 |
| | $AUC_{0-t}$ | 103.74 | 98.69-109.05 |
| | $AUC_{0-inf}$ | 103.65 | 98.28-109.31 |

While this invention has been described in detail with reference to certain preferred embodiments, it should be appreciated that the present invention is not limited to those precise embodiments. Rather, in view of the present disclosure, which describes the current best mode for practicing the invention, many modifications and variations would present themselves to those skilled in the art without departing from the scope, and spirit of this invention.

The invention claimed is:

1. A stable immediate release solid oral pharmaceutical composition consisting of:
   (a) from about 60 to 80% by weight Deferasirox or its pharmaceutically acceptable salts;
   (b) from about 10.0 to 40.0% by weight of one or more diluents;
   (c) from about 0.1% to 6.0% by weight of one or more binders;
   (d) from about 0.1% to 10.0% by weight of one or more disintegrants; and
   (e) from about 0% to 0.5% by weight of one or more surfactant; wherein the composition is free of glidant and is not in the form of a dispersible tablet.

2. The pharmaceutical composition of claim 1, wherein the composition has a bulk density of about 0.3 g/ml to 0.5 g/ml.

3. The pharmaceutical composition of claim 1, wherein the Deferasirox or its pharmaceutically acceptable salt is present in an amount of between about 60% to about 74% by weight.

4. The pharmaceutical composition of claim 1, wherein the one or more diluents is present in an amount of between about 18% to about 24.54% by weight.

5. The pharmaceutical composition of claim 1, wherein the one or more binders is present in an amount of between about 4.11% to about 5.29% by weight.

6. The pharmaceutical composition of claim 1, wherein the one or more disintegrants is present in an amount of between about 4.03% to about 7.6% by weight.

7. The pharmaceutical composition of claim 1, wherein the one or more surfactants is present in an amount of between about 0.12% to about 0.18% by weight.

8. The pharmaceutical composition of claim 1, wherein the one or more diluents is selected from the group consisting of calcium carbonate, calcium phosphate, dibasic anhydrous, calcium phosphate, dibasic dihydrate, calcium sulphate, silicified microcrystalline cellulose, cellulose acetate, compressible sugar, confectioner's sugar, dextrates, dextrose, fructose, lactitol, lactose, magnesium carbonate, magnesium oxide, maltodextrin, maltose, mannitol, microcrystalline cellulose, polydextrose, simethicone, sodium alginate, sodium chloride, sorbitol, sucrose, trehalose and xylitol, and mixtures thereof.

9. The pharmaceutical composition of claim 1, wherein the one or more binders is selected from the group consisting of acacia, alginic acid, carbomer, carboxymethylcellulose sodium, *ceratonia*, cottonseed oil, dextrin, dextrose, gelatin, guar gum, hydrogenated vegetable oil type 1, hydroxyethyl cellulose, hydroxyethyhnethyl cellulose, hydroxypropyl cellulose, low substituted hydroxypropyl cellulose, hypromellose, magnesium aluminium silicate, maltodextrin, maltose, methylcellulose, polydextrose, polyethylene oxide, povidone, sodium alginate, starch, stearic acid, sucrose and zein, and mixtures thereof.

10. The pharmaceutical composition of claim 1, wherein the one or more disintegrants is selected from the group consisting of alginic acid, carboxymethylcellulose calcium, carboxymethylcellulose sodium, croscarmellose sodium, crospovidone, docusate sodium, guar gum, low substituted hydroxypropyl cellulose, magnesium aluminium silicate, methylcellulose, povidone, sodium alginate, sodium starch glycolate, polacrilin potassium, silicified microcrystalline cellulose, pre-gelatinized starch, and mixtures thereof.

11. The pharmaceutical composition of claim 1, wherein the one or more surfactants is selected from the group consisting of sodium lauryl sulphate, sodium cetyl stearyl sulphate, sodium dioctyl sulphosuccinate, lecithin, cetyl alcohol, stearyl alcohol, cetyl stearyl alcohol, cholesterol, sorbitan fatty acid esters, polyoxyethylene sorbitan fatty acid esters, polyoxyethylene fatty acid glycerides, polyoxyethylene fatty acid esters, polyoxyethylene fatty alcohol ethers, glycerol fatty acid esters and mixtures thereof.

12. The composition of claim 1, wherein the composition exhibits an in-vitro dissolution rate of more than 85% of drug release within 20 minutes, when said dosage form is placed in a dissolution vessel filled with 900 ml of Phosphate Buffer, pH 6.8 having 0.5% Tween 20 maintained at 37+0.5° C. and stirred at a paddle speed of 75 rpm using a USP Type II (paddle) apparatus.

13. The composition of claim 1, wherein the composition comprises an extra-granular part and the extra-granular part is free of any binder.

14. The composition of claim 1, wherein the Deferasirox or its pharmaceutically acceptable salts is present in an amount ranging from about 50 to about 800 mg.

15. A process for the preparation of the pharmaceutical composition of claim 1, wherein the composition is in the form of granules or tablet and the process comprises:
    (a) blending a mixture of Deferasirox and at least one pharmaceutically acceptable excipient;
    (b) granulating said mixture using a suitable aqueous or non-aqueous solvent; and
    (c) optionally mixing with other pharmaceutical acceptable excipients to prepare a granule dosage form or optionally compressing the granules to form tablets.

16. An immediate release solid oral pharmaceutical composition consisting of:
    (a) from about 60 to 80% by weight Deferasirox or its pharmaceutically acceptable salts, wherein the Deferasirox or pharmaceutically acceptable salt is present in the composition in an amount ranging from about 50 to about 800 mg;
    (b) from about 10.0 to 40.0% by weight of one or more diluents;
    (c) from about 0.1% to 6.0% by weight of one or more binders;
    (d) from about 0.1% to 10.0% by weight of one or more disintegrants; and
    (e) from about 0% to 0.5% by weight of one or more surfactant; wherein the composition is free of colloidal silicon dioxide and tribasic calcium phosphate and is not in the form of a dispersible tablet.

17. The composition of claim 16, wherein the composition comprises an extra-granular part and the extra-granular part is free of any binder.

18. The composition of claim 16, wherein the composition exhibits an in-vitro dissolution rate of more than 85% of drug release within 20 minutes, when said dosage form is placed in a dissolution vessel filled with 900 ml of Phosphate Buffer, pH 6.8 having 0.5% Tween 20 maintained at 37+0.5° C. and stirred at a paddle speed of 75 rpm using a USP Type II (paddle) apparatus.

19. The pharmaceutical composition of claim 16, wherein:
    the Deferasirox or its pharmaceutically acceptable salt is present in an amount of between about 60% to about 74% by weight;
    the one or more diluents is present in an amount of between about 18% to about 24.54% by weight;
    the one or more binders is present in an amount of between about 4.11% to about 5.29% by weight;
    the one or more disintegrants is present in an amount of between about 4.03% to about 7.6% by weight; and
    the one or more surfactants is present in an amount of between about 0.12% to about 0.18% by weight.

* * * * *